United States Patent [19]

Lyons et al.

[11] Patent Number: 4,891,461

[45] Date of Patent: Jan. 2, 1990

[54] PROCESS FOR THE PRODUCTION OF AN ISOBUTENYLCYCLOHEXENE

[75] Inventors: David Lyons, Hull; Derek K. MacAlpine, Haywards Heath, both of England

[73] Assignee: BP Chemicals Limited, London, England

[21] Appl. No.: 164,834

[22] Filed: Mar. 7, 1988

[30] Foreign Application Priority Data

Mar. 10, 1987 [GB] United Kingdom ............... 8705564

[51] Int. Cl.$^4$ ............................................. C07C 2/02
[52] U.S. Cl. ...................................... 585/376; 585/375
[58] Field of Search ....................... 585/375, 376, 438

[56] References Cited

U.S. PATENT DOCUMENTS

| | | | |
|---|---|---|---|
| 3,192,278 | 6/1965 | Hastings et al. | 585/375 X |
| 3,728,407 | 4/1973 | Kubicek | 585/376 X |
| 3,728,414 | 4/1973 | Helden et al. | 585/346 |
| 3,751,498 | 8/1973 | Schmerling | 585/375 |
| 3,848,010 | 11/1974 | Intille | 585/438 |
| 4,022,846 | 5/1977 | Allen et al. | 585/438 X |
| 4,514,519 | 4/1985 | Hobbs | 502/243 |
| 4,547,617 | 10/1985 | Welch | 585/646 |

FOREIGN PATENT DOCUMENTS

| | | |
|---|---|---|
| 0196165 | of 1986 | European Pat. Off. . |
| 1263756 | 3/1968 | Fed. Rep. of Germany ...... 585/375 |
| 2018890 | of 1971 | Fed. Rep. of Germany . |

OTHER PUBLICATIONS

Usov, et al., "Disproportionation of Propylene" . . . Chem. Abstracts, vol. 81, No. 3, 22nd Jul., 1974, p. 293.
Nakamura et al., "The Role of $Me_xO_y$ in the . . . ", Receueil Trav. Chim. Pay-Bus, vol. 96, No. 11, 1977, pp. 731–734.
Soviet Inventions Illustrated Week 37, 24th Oct. 1984, Abs. No. 84–230359/37, Derwent Publications Ltd.

*Primary Examiner*—Patrick P. Garvin
*Assistant Examiner*—George R. Fourson
*Attorney, Agent, or Firm*—Nixon & Vanderhye

[57] ABSTRACT

An isobutenylcyclohexene (IBCH) is produced by reacting under disproportionation conditions an isoolefin with a vinylcyclohexene (VCH), or by reacting an isoolefin and a compound derivable from a VCH by homodisproportionation involving the elimination of ethylene, in the presence of a supported rhenium heptoxide disproportionation catalyst promoted with at least one transition metal in the form of the elemental metal and/or an oxide thereof, for example either copper or zinc.

4 Claims, No Drawings

PROCESS FOR THE PRODUCTION OF AN ISOBUTENYLCYCLOHEXENE

The present invention relates to a process for the production of an isobutenylcyclohexene (IBCH) by a disproportionation reaction of an isoolefin and a vinylcyclohexene (VCH), or of an isoolefin and a compound derivable from a VCH by homodisproportionation involving the elimination of ethylene, using as catalyst a supported rhenium heptoxide, and the conversion of an IBCH so-produced to an isobutylbenzene (IBB).

Isobutylbenzene itself is a high value speciality chemical used, for example, as an intermediate in the preparation of analgesics. Conventionally, isobutylbenzene is produced industrially by the side-chain alkylation of toluene with propylene using an alkali metal catalyst. The alkali metal catalyst can be a liquid potassium, a liquid potassium/sodium eutectic or an alkali metal supported on a diatomaceous earth, as disclosed in, for example, U.S. Pat. No. 3,449,455. The aforedescribed process has a number of disadvantages when operated commercially, since the alkali metal catalyst is (a) expensive, (b) inflammable and difficult to handle, and (c) short-lived owing to gum formation. In addition there is formed, as a by-product, substantial quantities of n-butylbenzene which has to be separated subsequently from the isobutylbenzene.

In our European application publication number 0196165 we describe a two stage process which avoids the problems associated with the alkylation route and allows the selective production of isobutylbenzene. The process comprises (1) in a first stage contacting a VCH and an isoolefin with a dismutation catalyst under dismutation conditions to produce an IBCH and another olefin, and (2) in a second stage contacting the IBCH produced in the first stage with a dehydroisomerisation catalyst at elevated temperature to produce the IBB. A preferred disproportionation catalyst for use in the first stage is rhenium heptoxide supported on alumina or a phosphated alumina. The use of supported rhenium heptoxide catalysts in disproportionation reactions is known from, for example, published GB Pat. Nos. 1054864, 1064829, 1106015, 1089956, 1103976, 1121806, 1123500, 1159055, 1159053, 1159056, 1170498 and 1279254. The use of a phosphated alumina catalyst is described for example in GB-A No. 1414488.

A general problem encountered with disproportionation catalysts is a tendency to catalyse the isomerisation of isomerisable olefinic hydrocarbons, thereby reducing the selectivity to desirable olefins by side-reaction disproportionation of the isomerised olefin. Another problem encountered in codisproportionation reactions is the tendency of disproportionation catalysts to catalyse homodisproportionation reactions and vice-versa, thereby again reducing the overall selectivity to the desired disproportionation product or products. In the specific case of the disproportionation reaction between 4-vinylcyclohexene (a VCH) and 2,4,4-trimethylpentene-2 (an isoolefin) to produce IBCH and 3,3-dimethylbutene-1(3,3DMB1), which may be represented as follows:

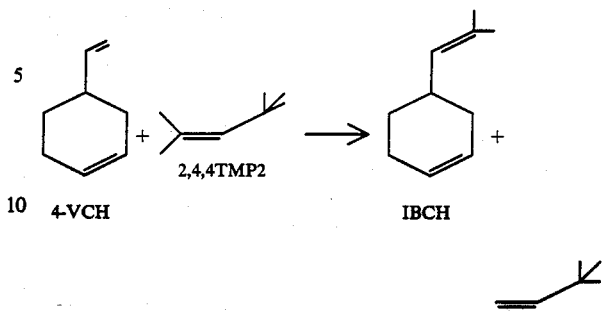

the efficiency of the reaction can be reduced by side-reactions principally by 4-VCH homodisproportionation to 1,2-dicyclohexenylethene (1,2DHE) and ethylene and/or 2,4,4TMP2 isomerisation to 2,4,4-trimethylpentene-1(2,4,4TMP1), which reactions may be represented as follows:

(a) 4-VCH Homodisproportionation

Although 1,2DHE may be used as a reactant, it is preferred to use a VCH and minimise the homodisproportionation reaction.

(b) 2,4,4TMP2 Isomerisation

We have now found that surprisingly, using a supported rhenium heptoxide as the disproportionation catalyst, the extent of these side reactions can be reduced by the use of at least one transition metal promoter.

Accordingly, the present invention provides a process for the production of an IBCH by reacting under disproportionation conditions an isoolefin with a VCH, or of an isoolefin and a compound derivable from a VCH by homodisproportionation involving the elimination of ethylene, in the presence of a supported rhenium heptoxide disproportionation catalyst *characterised in that* the catalyst is promoted with at least one transition metal in the form of the elemental metal and/or an oxide thereof.

The term 'transition metal' for the purpose of the present invention is defined as any metal capable of having more than one valency and having an incomplete d shell in at least one of its oxidation states. Transition metals include metals of Groups IB, IIB, IVA, VIIB and VIII of the Periodic Table of the Elements as published and copyrighted by Sargent-Welch Scientific Company of Skokie, Ill., USA. Examples of suitable transition metals include copper, zinc, nickel, tin, cobalt, manganese and palladium, of which copper, zinc, nickel, palladium and cobalt are preferred and copper and zinc are most preferred. The amount of the transition metal promoter may suitably be in the range from 1 to 15% w/w, based on the total weight of the supported rhenium heptoxide catalyst.

The support may be any refractory metal oxide, for example alumina, silica, silica-alumina, titania, zirconia, thoria, and the like. A preferred support is alumina and gamma-alumina is most preferred. The alumina may be used in phosphated form or in acid-treated form, or in any other form which facilitates the disproportionation reaction.

Examples of particularly useful catalysts for this reaction are gamma-alumina supported rhenium heptoxide/copper catalysts of the composition 6% w/w $Re_2O_7$ and 3–6% w/w copper and a gamma-alumina supported rhenium heptoxide/zinc catalyst of the composition 6% w/w $Re_2O_7$ and 3% w/w zinc, the copper and zinc being in the form of the elemental metal and/or an oxide thereof.

The support may be loaded with the transition metal by any of the methods conventionally employed for the production of supported metal catalysts and may be incorporated either before or after or together with the rhenium component. The transition metal is preferably incorporated into the supported rhenium heptoxide catalyst. A suitable method is to impregnate a supported rhenium heptoxide catalyst with a solution or solutions of one or more transition metals in the form of compound(s) thermally decomposable to the metal and/or oxide and thereafter thermally decomposing the compound(s) to the metal(s) and/or oxide(s). Impregnation is a commonly used technique for incorporating an active component on a support. Basically this procedure involves bringing the support into contact with a solution of a compound or salt and removing the excess solvent, usually by evaporation thereby effecting a drying of the catalyst. Thus the desired catalytic material is forced to extend throughout the pores and/or over the surface of the carrier and is totally transferred from the solution to the carrier.

The reaction resulting in the formation of an IBCH is between an isoolefin and a VCH or a compound derivable therefrom by homodisproportionation involving the elimination of ethylene.

The isoolefin reactant may suitably be of the formula:

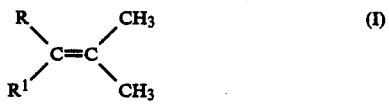

wherein R and $R^1$ are independently either hydrogen or hydrocarbyl groups. The hydrocarbyl radicals are suitably $C_1$ to $C_6$ alkyl groups. Preferred isoolefins are isobutene (R=$R^1$=H), 2,3-dimethylbutene-2 (R=$R^1$=$CH_3$), 2-methylbutene-2 (R=H; $R^1$=$CH_3$), 2-methylpentene-2 (R=H; $R^1$=$C_2H_5$) and 2,4,-trimethylpentene-2 (R=H, $R^1$=$C_4H_9$).

As the VCH there may be used any suitable VCH. Suitable VCHs include the vinylcyclohexa-mono-enes, of which 4-vinylcyclohexene is preferred since this is the most readily available. The cyclohexene ring of the VCH may be substituted with alkyl or aryl groups in which case substituted IBCHs are produced. Alternatively, there may be used a compound derivable from a VCH by homodisproportionation involving the elimination of ethylene, for example a DCHE, particularly when a symmetrical isoolefin, for example 2,3-dimethylbutene-2 is employed as the isoolefin reactant, because in this case only a single product is obtained in the disproportionation reaction. For example, when 1,2-dicyclohexenylethene is used, the reaction proceeds according to the equation:

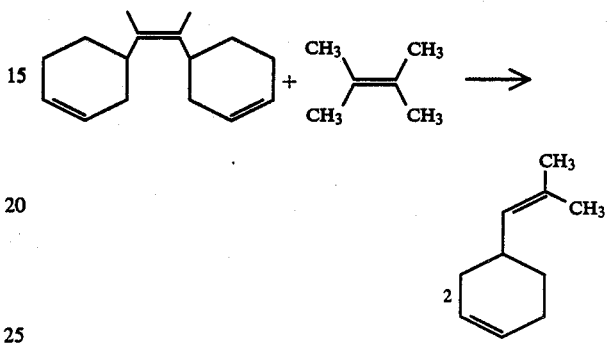

Another desirable reaction is that of 4-vinylcyclohexene and 2,4,4-trimethylpentene-2 to produce IBCH.

Although the VCHs posses two double bonds (one cyclic in the cyclohexene ring and one excocyclic outside the ring), it is only the excocylic double bond which undergoes disproportionation. This preference of the disproportionation catalyst for exocyclic double bonds means that the VCH can be carried using any VCH, for example a vinylcyclohexa-mono-ene, a vinylcyclohexa-di-ene or a vinylcyclohexa-tri-ene.

The conditions of temperature and pressure which effect disproportionation of the olefinic hydrocarbon feed may suitably be those conventionally employed for supported rhenium heptoxide catalysts, typically a temperature in the range from $-20°$ to $+500°$ C., preferably in the range from 10° to 100° C. and pressures in the range from atmospheric to 50 bar. The contact time of the feedstock on the catalyst may suitably lie in the range from 0.01 second to 120 minutes, preferably from 0.1 second to 60 minutes.

The process may be operated batchwise or continuously, using the catalyst in the form of a fixed bed, a fluidised bed or a moving bed.

In another aspect the present invention provides a process for the conversion of an IBCH produced as aforesaid to an IBB which process comprises contacting the IBCH with a catalyst, the catalyst being (i) a dehydroisomerisation catalyst when the cyclohexene moiety is a mono-ene, (ii) an isomerisation catalyst when the cyclohexene moiety is a di-ene and (iii) an isomerisation/hydrogenation catalyst when the cyclohexene moiety is a tri-ene, hydrogen being co-fed to the process when the catalyst is (iii).

Suitable dehydroisomerisation catalysts and reaction conditions for operating the conversion of IBCH to isobutylbenzene are given in our copending European Application Publication No. 196165 and in our copending European application No. (BP Case No. 6597) claiming priority from UK application No. BA 8705565 of 10, 1987 which describes a preferred manner of operating the conversion. The contents of these applications are incorporated by reference herein.

Suitable isomerisation catalysts (ii) and hydrogenation catalysts (iii) and conditions for their efficient operation will be well known to those skilled in the art.

The process of the present invention will now be further illustrated by reference to the following Examples.

CATALYST PREPARATION

Catalyst A - 6% $Re_2O_7$/gamma-$Al_2O_3$

To 100 g of 300–500 micron particle size gamma-alumina (based on Catapal SB pure boehmite) was added 100 ml of an aqueous solution of 7.1 g ammonium perrhenate. The mixture was impregnated at 80° C. for 6 hours, during which it was kept moist by the occasional addition of deionised water. It was then dried at 80° C. for 1 hour, then at 100° C. in vacuo for 8 hours. The catalyst was then activated at 580° C. in flowing air.

Catalyst B - 6% $Re_2O_7$/6% Cu/gamma-$Al_2O_3$

To 5 g of Catalyst A was added 10 ml of an aqueous solution of 1.44 g of copper (II) nitrate. The mixture was impregnated and dried as for Catalyst A. The catalyst was then activated in flowing air using the following temperature programme: 150° C., 170° C., 200° C., 300° C., 400° C., 500° C. each for 1 hour and then 580° C. for 16 hours.

Catalyst C - 6% Cu/6% $Re_2O_7$/gamma-$Al_2O_3$

To 10 g of 300–500 micron particle size gamma-alumina was added 15 ml of an aqueous solution of 2.97 g of copper (II) nitrate. The mixture was impregnated and dried as for Catalyst A. The catalyst was activated as for Catalyst B. To the activated catalyst, 9.81 g, was then added 10 ml of an aqueous solution of 0.7 g of ammonium perrhenate. The mixture was impregnated, dried and activated as for Catalyst A.

Catalyst D - 6% $Re_2O_7$/3% Cu/gamma-$Al_2O_3$

To 10 g of 300–500 micron particle size gamma-alumina was added 10 ml of an aqueous solution of 0.71 g of ammonium perrhenate and 1.44 g of copper (II) nitrate. The mixture was impregnated, dried and activated as for Catalyst B.

Catalyst E - 6% $Re_2O_7$/3% Cu/gamma-$Al_2O_3$

To 5 g of Catalyst A was added 10 ml of an aqueous solution of 0.77 g of copper (II) nitrate. The mixture was impregnated, dried and activated as for Catalyst B.

Catalyst F - 6% $Re_2O_7$/3% Zn/gamma-$Al_2O_3$

To 10.2 g of Catalyst A was added 20 ml of an aqueous solution of 1.44 g of zinc (II) nitrate. The mixture was impregnated, dried and activated as for Catalyst A.

Catalyst G - 6% $Re_2O_7$/3% Ni/gamma-$Al_2O_3$

To 10 g of Catalyst A was added 10 ml of an aqueous solution of 1.5 g of nickel (II) nitrate. The mixture was impregnated and dried as for Catalyst A. The catalyst was then activated in flowing air using the following temperature programme: 50° C. for 1 hour, 120° C. for 4 hours, 200° C. for 1 hour, 580° C. for 16 hours.

Catalyst H - 3% Ni/6% $Re_2O_7$/gamma-$Al_2O_3$

To 10 g of 300–500 micron gamma-alumina was added 20 ml of an aqueous solution of 1.53 g of nickel (II) nitrate. The mixture was impregnated and dried as for Catalyst A. The catalyst was activated as for Catalyst G. To the activated catalyst, 9.68 g, was added 20 ml of an aqueous solution of 0.68 g of ammonium perrhenate. The mixture was impregnated, dried and activated as for Catalyst A.

Catalyst I - 6% $Re_2O_7$/3% Sn/gamma-$Al_2O_3$

To 5 g of Catalyst A was added 0.31 g of tin (II) acetate. The mixture was thoroughly mixed and then heated to 100° C. under vacuum for 16 hours.

Catalyst J - 6% $Re_2O_7$/3% Mn/gamma-$Al_2O_3$

To 5 g of Catalyst A was added 10 ml of an aqueous solution of 0.81 g of manganese (II) nitrate. The mixture was impregnated and dried as for catalyst A. The catalyst was then activated in flowing air using the following temperature programme: 100° C. for 4 hours, 200° C. for 1 hour and 580° C. for 19 hours.

Catalyst K - 6% $Re_2O_7$/3% Pd/gamma-$Al_2O_3$

To 10.97 g of Catalyst A was added 50 ml of an aqueous solution of 0.63 g of palladium (II) nitrate. The mixture was impregnated and dried as for Catalyst A. The catalyst was activated in flowing air at 580° C. for 24 hours.

Catalyst L - 6% $Re_2O_7$/3% Co/gamma-$Al_2O_3$

To 5 g of Catalyst A was added 10 ml of an aqueous solution of 0.76 g of cobalt (II) nitrate. The mixture was impregnated and dried as for Catalyst A. The catalyst was activated in flowing air using the following temperature programme: 350° C. for 8 hours and 580° C. for 16 hours.

EXAMPLES 1-11 AND COMPARISON TEST

Each of the catalysts A to L were tested by feeding a 10:1 (molar) mixture of 2,4,4TMP2 and 4-VCH over them at 18° C., Liquid Hourly Space Velocity (LHSV)=1.

The initial conversions, selectivities and isomerisations are shown in the Table.

TABLE

| Example | Catalyst | Transition Metal | 4-VCH Conversion (%) | 4-VCH Selectivity to IBCH (%) | Isomerisation of 2,4,4 TMP2 to 2,4,4 TMP1 (%) |
|---|---|---|---|---|---|
| Comp Test | A | — | 80.0 | 63.0 | 20.0 |
| 1 | B | Cu | 98.0 | 75.0 | 0.5 |
| 2 | C | Cu | 98.7 | 77.4 | 0.82 |
| 3 | D | Cu | 98.3 | 72.24 | 4.47 |
| 4 | E | Cu | 95.9 | 68.2 | 1.4 |
| 5 | F | Zn | 90.1 | 71.7 | 3.2 |
| 6 | G | Ni | 90.0 | 70.2 | 8.2 |
| 7 | H | Ni | 88.6 | 62.9 | 20.9 |
| 8 | I | Sn | 88.2 | 66.5 | 20.9 |
| 9 | J | Mn | 85.2 | 68.2 | 8.6 |
| 10 | K | Pd | 77.1 | 61.7 | 5.7 |
| 11 | L | Co | 74.8 | 58.7 | 6.6 |

The Comparison Test using Catalyst A is not an example according to the present invention because no transition metal promoter was used. It is included only for the purpose of comparison.

The results in the Table demonstrate the effectiveness of transition metal promoters in increasing the activity of a gamma-alumina supported rhenium heptoxide catalyst and/or reducing side-reaction activity.

We claim:

1. A process for the production of an isobutenylcyclohexene by reacting under disproportionation conditions 2,4,4-trimethylpentene-2 and 4-vinylcyclohexene in the presence of a supported rhenium heptoxide disproportionation catalyst, said catalyst being promoted with at least one transition metal promoter selected from the group consisting of copper and zinc and extending throughout the pores of the support or over the surface of the support, said transition metal promoter being in the form of the elemental metal or an oxide thereof.

2. A process according to claim 1, wherein the total amount of transition metal promoter is in the range of from 1 to 15% by weight, based on the total weight of the supported rhenium heptoxide catalyst.

3. A process according to claim 1, wherein the support is gamma-alumina.

4. A process according to claim 1, wherein the disproportionation conditions are a temperature in the range of from 10° to 100° C. and a pressure in the range of from atmospheric to 50 bar.

* * * * *